United States Patent [19]
Ortloff et al.

[11] Patent Number: 5,740,863
[45] Date of Patent: Apr. 21, 1998

[54] SUBSEA WELLHEAD MECHANICAL EROSION DETECTOR

[75] Inventors: Charles R. Ortloff; Thomas James Dorsch, both of Los Gatos, Calif.; Lee A. Gillette; John Charles Vicic, both of Spring, Tex.; Michael R. Williams, Houston, Tex.

[73] Assignee: FMC Corporation, Chicago, Ill.

[21] Appl. No.: 646,822

[22] Filed: May 21, 1996

[51] Int. Cl.$^6$ ............................................. G01N 17/00
[52] U.S. Cl. ....................................... 166/368; 73/86
[58] Field of Search ........................ 73/86, 152.01; 166/368, 902

[56] References Cited

U.S. PATENT DOCUMENTS

| | | | |
|---|---|---|---|
| 2,994,778 | 8/1961 | Marsh | 73/86 |
| 3,639,876 | 2/1972 | Wilson | 73/86 X |
| 3,753,257 | 8/1973 | Arnold | 166/66 X |
| 4,131,815 | 12/1978 | Boatright | 73/152.18 |
| 4,389,877 | 6/1983 | Lacey | 73/86 X |
| 4,389,880 | 6/1983 | Robinet | 73/86 |
| 4,442,706 | 4/1984 | Kawate et al. | 73/86 |
| 4,481,809 | 11/1984 | LaBate | 73/86 |
| 4,768,373 | 9/1988 | Spencer | 73/86 |
| 4,779,453 | 10/1988 | Hopenfeld | 73/86 |
| 5,211,677 | 5/1993 | Sargeant et al. | 73/61.71 |
| 5,495,752 | 3/1996 | Townsend | 73/86 |
| 5,571,955 | 11/1996 | Beavers et al. | 73/86 |

*Primary Examiner*—William P. Neuder
*Attorney, Agent, or Firm*—Henry C. Query, Jr.

[57] ABSTRACT

A consumable probe is installed in an elbow zone of a well. The consumable probe is subject to ablation caused by abrasive particles suspended in the fluid being transported by the conduit. As the probe is ablated pressure sensitive chambers will be exposed and the pressure in the conduit will pressurize the pressure sensitive chambers and signal a readout station in a position remote from the location of the probe in the conduit.

3 Claims, 4 Drawing Sheets

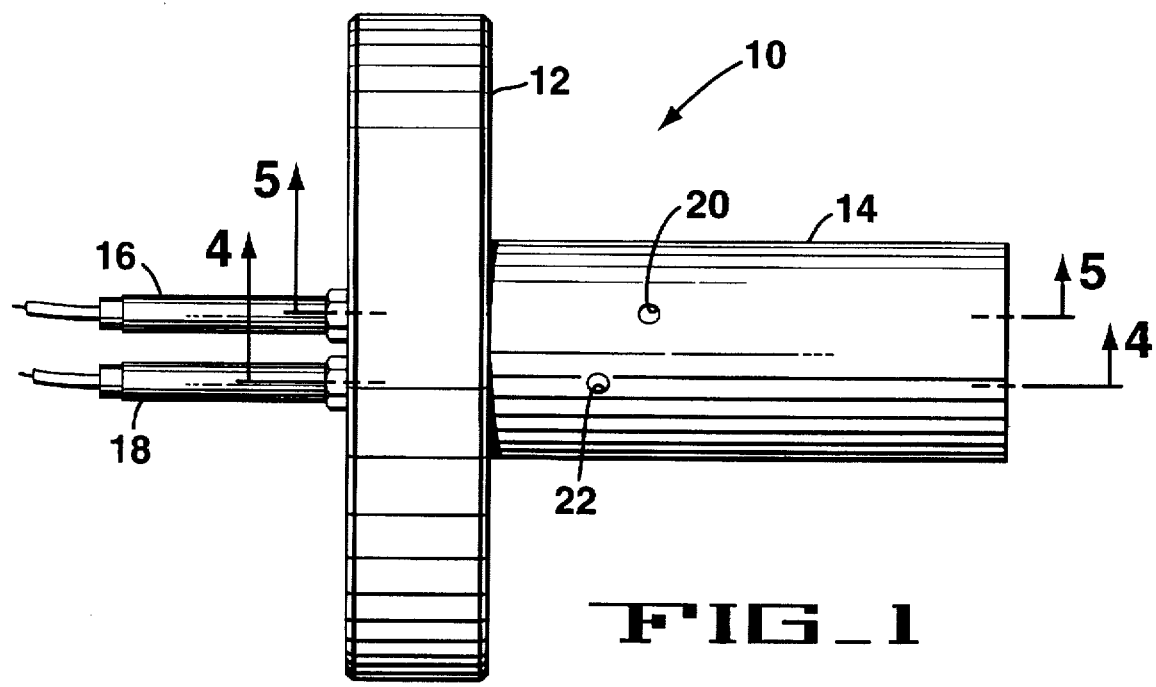
FIG_1
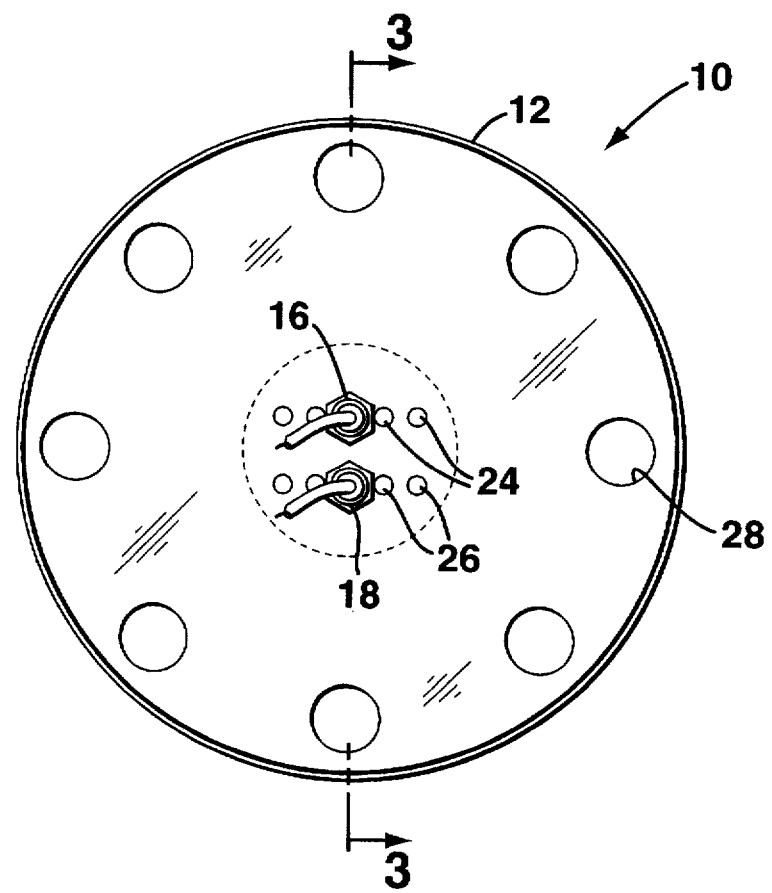
FIG_2

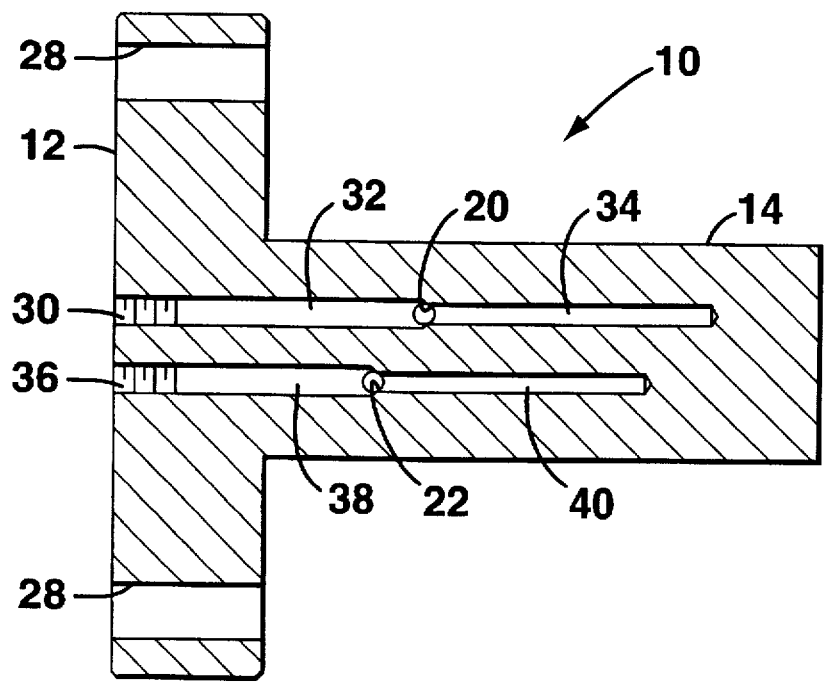
FIG_3
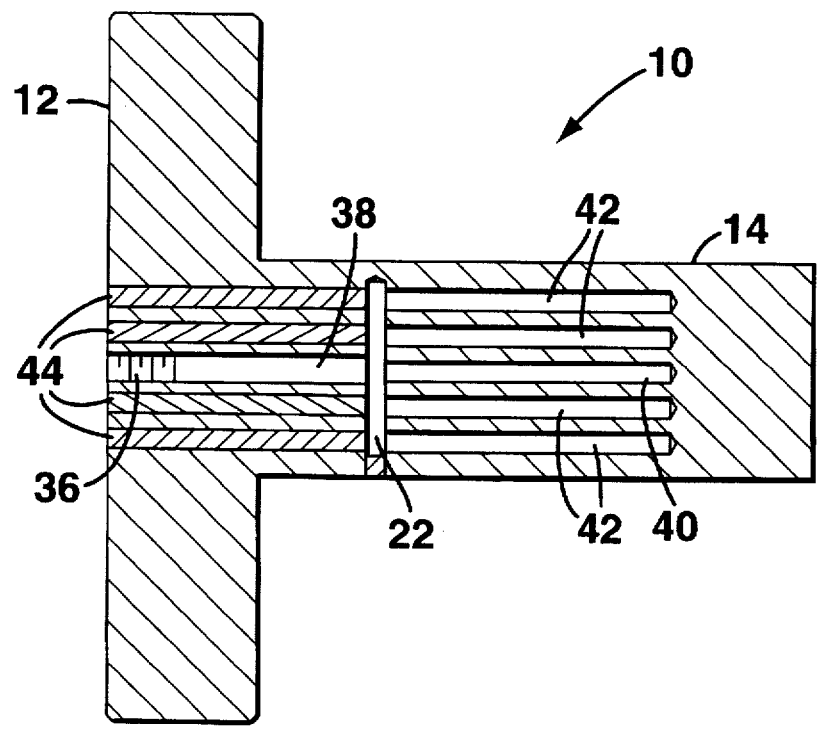
FIG_4

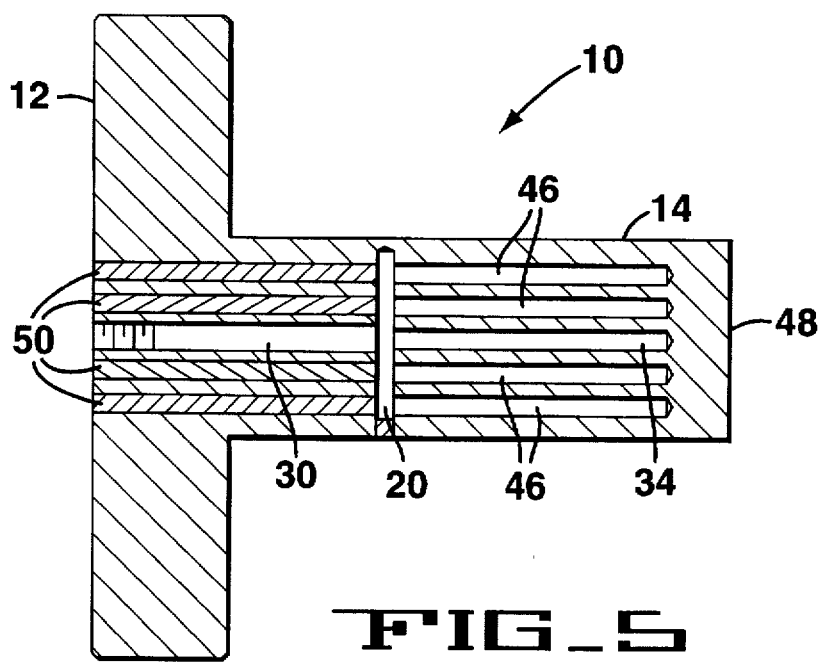
FIG_5
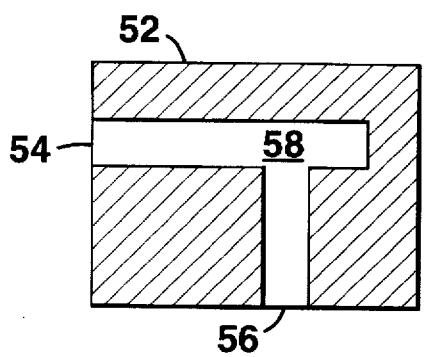
FIG_6
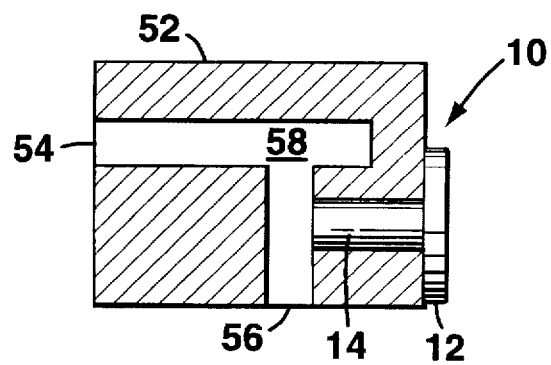
FIG_7
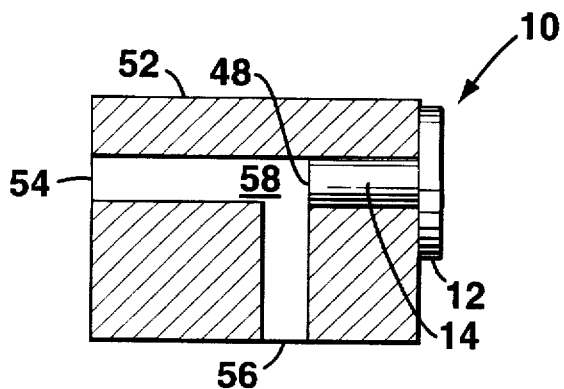
FIG_8
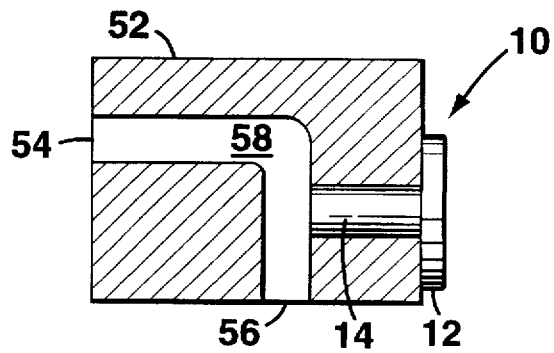
FIG_9

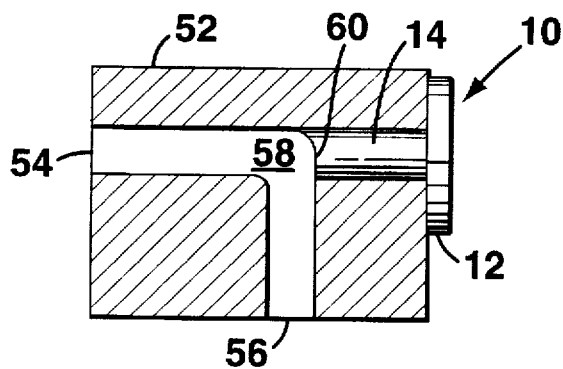
FIG_10
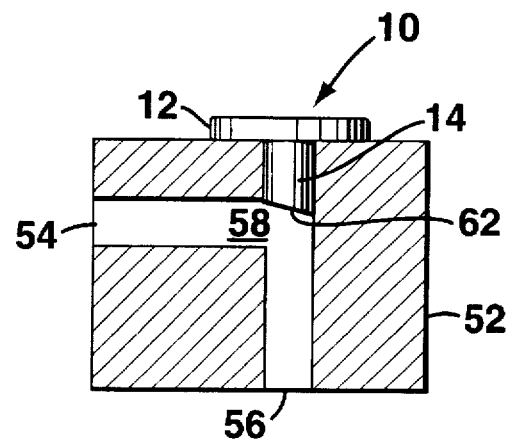
FIG_11
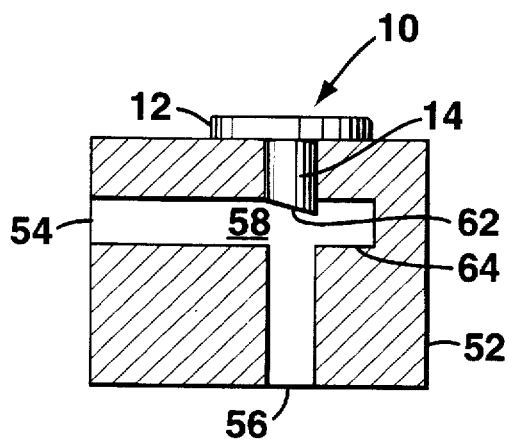
FIG_12
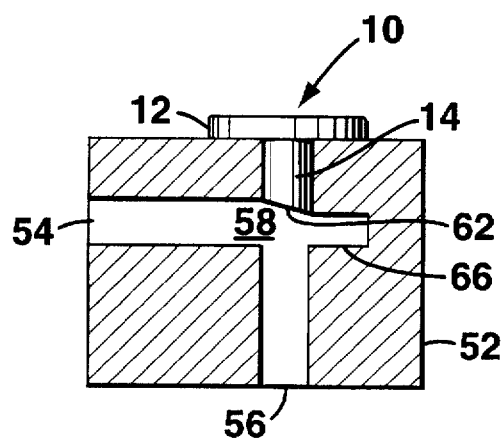
FIG_13

SUBSEA WELLHEAD MECHANICAL EROSION DETECTOR

BACKGROUND OF THE INVENTION

1. Field of the Invention

This invention has to do with apparatus for use in oil and gas well completion equipment and specifically to a method of detecting sand in a stream of gas being extracted from a well. The detection is made possible by means of a consumable apparatus, namely a probe having an erodable end surface contact zone that is exposed to the stream of gas at the wellhead preferably in the vicinity of an elbow.

2. Description of the Prior Art

It has been known that sand or other abrasive materials in a gas stream have very serious effects on the plumbing systems of wellhead equipment. Traditionally, if sand were found in a gas stream it was found once the gas had traveled from the wellhead to a collection point remote from the wellhead. With the discovery of the sand the well would be shutdown to correct the problem by well known downhole remedial measures. Sometimes however the time it took to discover the problem was too long to prevent damage to the wellhead due to the sand caused erosion and the ablation of the interior metal surfaces of valves, pipes, elbows, sensors and other wellhead and fluid transportation systems.

One method of sensing erosion in a well conduit was the use of a probe that intruded into the stream of fluid being transported by the pipe or other plumbing. These detectors are electrical devices that apparently change there electrical signal output as they are eroded away. The difficulty with these devices is that they are positioned in the interior of the conduit and may provide an impediment to fluid or items traveling through the conduit or may otherwise be subjected to damage not a function of erosion.

Another method of detecting wear is to have a special spool piece in the line. As the interior wall of the spool piece is eroded the diameter of the interior will be measured and when the wear is critical responsive action could be taken. The disadvantage of this type of detector is that the replacement of the spool piece is difficult as two end flanges need to be uncoupled and reconnected with the new spool piece.

SUMMARY OF THE INVENTION

The invention presented here is designed to give an early warning to well operators that there is sand being extracted from the well with gas product. The early warning is conveyed to the operator by means of a signal emanating from a single and from a second pressure transducer connected to a special fitting, in this case an erosion detector, at the wellhead. The first pressure transducer is in communication with a normally closed chamber of a given static pressure. In the event that the normally closed chamber is breached, for instance by the exterior of the chamber being eroded away or ablated by sand or other abrasive substances, the now compromised chamber will see pressure different from the static pressure in the chamber. This pressure will be close to the pressure in the well and thus could be much higher then the static pressure in the sensor passages of the erosion probe. The pressure differential will be sensed by the pressure transducers and generate the electrical signal useful in making people or equipment, including a computer based monitoring element, aware of the problem.

A second normally closed collection of sensor passages may be used to augment the action of the first set of sensor passages. This second set of sensor passages will operate in the same fashion as the first set of sensor passages but will provide a rate of wear measurement component to the system. When a second set of sensor passages and second pressure transducer system is used the time interval between the breech of the first set of sensor passages and breach of the second set of sensor passages will be recorded. The thickness of the material at the probe end of the erosion detector between the first set of sensor passages and the second set of sensor passages is known so given the time it takes to wear through this layer of material a simple algorithm can be solved to show the rate of wear. If the rate is fast the well can be immediately shut down. If the wear is slow then options to shut down or a controlled shut down can be accomplished.

In the simplest embodiment of this invention the inventors contemplate using a block of material of significant wall thickness, the block containing, but not limited to, an inlet passage, an outlet passage and an elbow between them. A bore will be formed in the block in line to intercept one of the passages or the elbow. The depth of the bore will be specified to end within a known distance from the passages or elbow. The bore will be fitted with a pressure transducer and the bore sealed with a provision for having the leads of the transducer communicating with a monitoring station. In this embodiment the erosion of the passage in the vicinity of the bore will eventually erode through the unbored portion between the passage and the bore and the pressure in the passage will be sensed by the pressure transducer thus sensing that there has been erosion in the passage. This embodiment requires the replacement of the entire block (or a rebuilding thereof) after breach. The other embodiments presented in this disclosure use replaceable probes that eliminate the need of replacing the entire block upon erosive breakthrough.

BRIEF DESCRIPTION OF THE DRAWINGS

The objects and advantages of the present invention will be more readily apparent from consideration of the following detailed description of the drawings which illustrate a preferred embodiment and several alternative embodiments of the invention.

In the Drawing Figures:

FIG. 1 is a side elevation view of the erosion detector presented herein;

FIG. 2 is a view of the end of the erosion detector looking from the pressure transducer end of the erosion detector;

FIG. 3 is a cross sectional view through 3—3 of FIG. 2;

FIG. 4 is a cross sectional view through 4—4 of FIG. 1;

FIG. 5 is a cross sectional view through 5—5 of FIG. 1;

FIG. 6 is a pictorial representation of a sectional view of blocked tee elbow in a housing;

FIG. 7 is a pictorial representation of a sectional view of a blocked tee with an erosion detector;

FIG. 8 is a pictorial representation of a sectional view of an elbow having an erosion detector inserted in the turning zone of the elbow;

FIG. 9 is a pictorial representation of a sectional view of a smooth radius elbow having an erosion detector inserted at the discharge side of the elbow;

FIG. 10 is a pictorial representation of a sectional view of an elbow with a modified erosion detector inserted in the turning zone of the elbow;

FIG. 11 is a pictorial representation of a sectional view of an elbow with a modified erosion detector inserted into the turning zone of the elbow;

FIG. 12 is a pictorial representation of a sectional view of a blocked tee having a modified erosion detector inserted into the turning zone of the passage;

FIG. 13 is a pictorial representation of a sectional view of a blocked tee having a modified erosion detector inserted into the turning zone of the passage and a modified passage formed to modify flow of fluid in the vicinity of the modified erosion detector.

DESCRIPTION OF THE PREFERRED EMBODIMENT

The invention will be understood by reading the following description of the preferred embodiment of the invention while perusing the drawing figures.

A side elevation view of the invention is shown in FIG. 1. Here the erosion sensor generally 10 is shown as having an attachment flange portion 12 and a probe portion 14. A pair of pressure transducer housings, 16 and 18, are shown. These pressure transducers, 16 and 18, are associated with cavities in and through the flange 12 and probe 14 as will be explained further on. Electrical conduit will connect these pressure transducers to a monitor generally located a distance away from the wellhead installation. First and second blocked cross drilled ports 20 and 22 respectively are provided in the probe to provide internal passages in the probe 14.

FIG. 2 is an elevation view of the pressure transducer side of the erosion sensor generally 10 showing the end view of the pressure transducers 16 and 18. Each pressure transducer is associated with a plurality of blocked passages such as the first set of blocked passages 24 and a second set of blocked passages 26. Flange attachment through bores, one shown as 28, are also shown in FIG. 2.

The critical elements of the erosion sensor 10 are clearly shown in FIGS. 3–5. Specifically, looking first at FIG. 3, the first primary passage 30 including a collector section 32, the first cross drilled port 20, and one of a first set of a plurality of sensor passages 34 and 46. A second primary passage 36, which includes a collector section 38, the second cross drilled port 22 and one of a second set of a plurality of sensor passages 40 and 42.

The second set of sensor passages, such as passages 42 (FIG. 4) and the passage 40 are represented through the section taken through 4—4 of FIG. 1. The five passages, are manifolded together by means of the second cross drilled port 22 which has been blocked after drilling, such that all five passages are connected to the collector section 38 of the second primary passage 36. As can be seen in this FIG. 4 the passages can be drilled from the flange 12 end of the erosion sensor 10 with the bores or sensor passages 42 blocked as shown at 44. Drilling these bores or passages from the extreme end of the probe is possible but may not be as desirable as this would be the erosion measuring surface of the erosion sensor.

FIG. 5 shows the first set of sensor passages 46, these being longer, that is extending further into the probe 14, to a zone closer to the relative inboard end 48 of the erosion probe. The sensor passage 34 can be thought of as one of the first set of sensor passages. All five of these sensor passages, 46 and 34, are manifolded together by means of the cross drilled port 20 that is blocked after drilling. This manifold 20 also connects to the first primary passage 30. The passages 46 are blocked as shown at 50.

The first and second set of sensor passages are similar with one set, the first set 46 and 34 being relatively longer than the second set of sensor passages 42 and 40.

As shown in FIGS. 2 and 3 the first and the second sets of sensor passages can be arrayed in horizontal planes as shown. Alternatively, the first and second sets of sensor passages can be arrayed in any number of different configurations, the critical element being that there is a difference in thickness between the anticipated break through points if each set, and there may be more then two sets of sensor passages.

The elbow containing block 52, pictorially represented in FIGS. 6–13 is a part of a wellhead assembly that is used to control flow from a well. The erosion detector 10, with its probe section 12, is a replaceable element that is expected to be partially consumed in the performance of its function—determination of abrasive material in a gas stream by measuring the rate of erosion or ablation in a particular section of a wellhead.

The operation, in principle, of the erosion detection device, explained as well further on in this specification, can be learned from FIGS. 3, 4 and 5 in the embodiments shown by FIGS. 7–13. With the flow, normally a stream of gas, flowing into the first leg leading to the elbow turn zone 58 in the block, its impingement on the contact surface 48, such as in FIG. 8, is generally non-destructive.

If the gas well malfunctions and abrasive material such as sand is carried with the high velocity stream of gas, the mixture of gas and sand will ablate the contact surface 48. Over time, sometimes over a short period of time, the abrasive mixture will erode or ablate the metal of the contact surface 48 to the degree that the first set of sensor passages, at least one of them, will be exposed. This will cause a pressure increase in this sensor passage and the first pressure passage 30 with a resultant signal being outputted from the first pressure transducer 16 which is in communication with the first primary passage 30. The signal from the first pressure transducer 16 will be directed to a monitoring station, which could be a computer terminal, for subsequent notification or action by a person or a machine.

If there is significant sand contaminated gas flow through the passage in the block 52 more depth or material will be eroded or ablated from the contact surface 48. In the context of this application the "contact surface" is that surface that is or becomes exposed to the fluid flow either immediately or eventually. Eventually the second set of sensor passages 42, or at least one of them, will be breached. Like the breach or break through of the first set of sensor passages 46, the breach or break through of this second set of sensor passages 42 will cause the pressure in the collector section 38 of the probe to be sensed by the second pressure transducer 18 and communicated by wire to a monitoring station or computer terminal remote from the location of the erosion detection device.

Returning to the specific figures associated with this specification several different configurations and embodiments of the invention are illustrated. It has been found that erosion in a pipeline and the attendant plumbing, such as in elbows, is not always at its maximum rate of erosion in the most obvious wear zones. It is usually expected that the outer radius of an elbow would see the greatest rate of wear. Through tests conducted by the inventors several zones of high expected wear have been identified. These zones of wear do include the elbow area of the passages but also include the zone downstream of the elbow zone. Furthermore the shape of the elbow zone, i.e. using a blocked tee arrangement will have significant affect on the wear pattern in the elbow turning zone. Selection of the position of the wear sensor to generate the greatest sensitivity to measuring erosion rate is critical to optimize the performance of the sensor. By having the ability to measure erosion rates accurately the predication of erosion rates in other or critical areas of the pipeline are possible. Insertion of the erosion detector disclosed herein into these zones is one aspect of this invention. These embodiments are shown in the drawing figures.

For instance, FIG. 6 presents a schematic elbow 52 that would be encountered in a fluid flowing assembly of pipes, valves and controls. In this diagrammatic presentation, and in FIGS. 7-13 flow will enter at inlet 54 and exit at port 56. The embodiment shown in FIG. 6 is a "blocked tee" configuration which is known to reduce erosion wear in a conventional elbow. The elbow zone in this figure is zone 58.

FIG. 7 shows the erosion sensor generally 10, having a probe section 14 and a flange section 12 as shown in FIG. 1. In this embodiment the erosion sensor 10 is downstream of the elbow 58. With the erosion sensor in this location the erosion of the zone beyond or downstream from the elbow 58 can be detected. The probe 14 will be as shown in FIGS. 1-5.

In FIG. 8, the erosion detector, generally 10, as illustrated in FIGS. 1-5, is positioned so that the relative inboard end 48 is in line with the elbow zone 58.

FIG. 9 shows a curved corner elbow 58 with the erosion sensor probe portion 14 downstream of the elbow zone 58 in an area of anticipated erosion. This will allow erosion detection downstream of the elbow turning zone 58.

FIG. 10 is similar to FIGS. 8 and 9 as the erosion detector generally 10 is directly in line with the input leg of the elbow and the elbow is curved. The probe portion 14, supported as usual by the flange 12 is equipped with a partially curved relative inboard end 60 to provide and otherwise match the curve of the elbow. This modified curved inboard end of the probe will function in a way similar to the FIG. 1 device.

FIG. 11 presents an alternative probe 14 configuration. The erosion detector 10 with the flange 12 supports the probe 14 at the outside radius of the elbow, however, the surface 62 is an angled surface inclined to form a diagonal from the inlet side leg of the elbow to the outlet side leg of the elbow. In this embodiment erosion detection will take place at the outboard radius of the elbow.

FIG. 12 uses the probe 14 of FIG. 11 with inclined surface 62 inserted into a "blocked tee" configuration with the cavity 64 downstream of the erosion detector generally 10.

FIG. 13 uses the erosion detector of FIGS. 11 and 12 with the angled surface 62 inserted into a modified blocked tee. In this modification the cavity portion 66 is smaller in diameter than the inlet side leg of the block. This smaller cavity is sized to fit the depth of the long side of the probe as defined by the surface 62. This eliminates the void area behind the probe in the cavity 64 of FIG. 12.

In summary, in the most simple embodiment of the invention, a detector means for the detection of abrasive material being carried by fluid passing through a wellhead is provided. It includes an erosion block having a passage therein and a bore intercepting the passage. A probe is inserted into the bore of the erosion block, this probe exposed to the passage when the probe is inserted in the bore. There is, as part of the probe, a set of first sensor passages in the probe inboard from the end of the probe. This first set of sensor passages will communicate with a first primary passage. A first pressure transducer means is provided for sensing pressure in the first primary passage and in the set of first sensor passages connected thereto. This pressure transducer provides an electrical output indicative of a change in pressure in the first primary passage and is electrically coupled to a means for responding to the electrical output of the first pressure transducer.

After the first set of sensor passages has been breached continued wear of the relative inboard end of the probe will cause the breach of the second set of sensor passages. This set of extension passages will communicate with a second primary passage. A second pressure transducer means is provided for sensing pressure in the second primary passage and in the set of second sensor passages connected thereto. This pressure transducer provides an electrical output indicative of a change in pressure in the second primary passage and is electrically coupled to a means for responding to the electrical output of the second pressure transducer.

By noting the time that the first set of sensors was breached and subtracting that from the time that the second set of sensors was breached the monitor can determine, given the known thickness of the probe material from the outboard end of the first set of sensors to the outboard end of the second set of sensors, the rate of erosion in the area or zone of the erosion sensor. If the rate is rapid the monitor can initiate the shutdown of the well until the cause of erosion can be eliminated.

The foregoing description, when read in conjunction with a perusal of the drawing figures, shows how the implementation of a erosion detection system that can be and is used to met the objects of the invention. The following claims seek to protect the inventor's idea by claiming the erosion detection principle in a manner that captures the spirit of the invention. Minor deviations and nuances of the invention are contemplated as being covered by the following claims.

What is claimed is:

1. An ablation detector for use in a fluid transmission conduit which is used to transmit fluid under pressure, the fluid being capable of ablating the conduit, the improvement comprising:

a wall surface for contacting the fluid in the transmission conduit;

a first cavity means separated from the fluid in the transmission conduit by the wall surface, the first cavity means being pressurized by the pressure in the transmission conduit when the fluid ablates at least a portion of the wall surface to expose the first cavity means;

wherein the pressure in the first cavity means actuates a pressure responsive signal means at a point in time for signaling pressure in the first cavity means;

a second cavity means separated from the fluid in the transmission conduit by the wall surface, the second cavity means being separate from said first cavity means and being pressurized by the pressure in the transmission conduit when the fluid ablates at least a portion of the wall surface to expose the second cavity means.

2. The invention in accordance with claim 1 wherein the dimension defined between the wall surface and the first cavity means is less than the dimension defined between the wall surface and the second cavity means.

3. The invention in accordance with claim 2 wherein the pressure in the second cavity means actuates a pressure responsive signal means at a point in time for signaling pressure in the second cavity means.

* * * * *